US010105145B2

(12) United States Patent
Lavallee

(10) Patent No.: US 10,105,145 B2
(45) Date of Patent: Oct. 23, 2018

(54) METHOD FOR CONSTRUCTING A PATIENT-SPECIFIC SURGICAL GUIDE

(71) Applicant: ORTHOTAXY, La Tronche (FR)

(72) Inventor: Stephane Lavallee, St. Martin d'Uriage (FR)

(73) Assignee: ORTHOTAXY, La Tronche (FR)

(*) Notice: Subject to any disclaimer, the term of this patent is extended or adjusted under 35 U.S.C. 154(b) by 588 days.

(21) Appl. No.: 14/667,623

(22) Filed: Mar. 24, 2015

(65) Prior Publication Data
US 2016/0279877 A1 Sep. 29, 2016

(51) Int. Cl.
B29C 67/00 (2017.01)
G05B 19/40 (2006.01)
A61F 2/38 (2006.01)
A61B 17/15 (2006.01)
B33Y 80/00 (2015.01)
B33Y 50/00 (2015.01)
A61B 17/17 (2006.01)
(Continued)

(52) U.S. Cl.
CPC ............. A61B 17/15 (2013.01); A61B 17/17 (2013.01); B29C 64/386 (2017.08); B33Y 50/00 (2014.12); B33Y 80/00 (2014.12); A61B 2017/00526 (2013.01); A61F 2240/002 (2013.01); B33Y 50/02 (2014.12)

(58) Field of Classification Search
CPC ....... B29C 67/00; B29C 67/0088; A61F 2/38; A61F 2/389; G05B 19/4099
See application file for complete search history.

(56) References Cited

U.S. PATENT DOCUMENTS 8,092,465 B2    1/2012  Metzger et al.
2007/0288030 A1* 12/2007 Metzger ............... A61B 17/154
                                                        606/87
(Continued)

FOREIGN PATENT DOCUMENTS

WO    WO-9325157    6/1993
WO    WO-2014/074042    11/2012

Primary Examiner — Christopher Beccia
(74) Attorney, Agent, or Firm — Womble Bond Dickinson (US) LLP

(57) ABSTRACT

The invention relates to a method for constructing a patient-specific surgical guide comprising at least one contact element comprising a contact surface intended to match an anatomical structure to be treated in view of implantation of an implant and at least one guiding element for guiding a surgical instrument to treat said anatomical structure, said method comprising:
  receiving a non-segmented 3D medical image of the anatomical structure of the patient;
  determining, in said non-segmented 3D medical image, anatomical references of the patient;
  based on said anatomical references, positioning an implant model in the non-segmented 3D medical image;
  adjusting at least one of: a type, a size, a position and an orientation of the implant model with respect to the anatomical structure in the non-segmented 3D medical image;
  recording planning data including said adjusted type, size, position and orientation of the implant model;
  using a patient-specific surgical guide adapted to carry out implantation of the implant, said patient-specific surgical guide being constructed using the planning data.

19 Claims, 3 Drawing Sheets

(51) Int. Cl.
  *B29C 64/386* (2017.01)
  *B33Y 50/02* (2015.01)
  *A61B 17/00* (2006.01)

(56) References Cited

U.S. PATENT DOCUMENTS

2009/0138020 A1     5/2009  Park et al.
2010/0191244 A1*    7/2010  White ............... A61B 17/155
                                                606/88
2013/0166256 A1*    6/2013  Wirx-Speetjens ...... G06F 17/50
                                                703/1

* cited by examiner

METHOD FOR CONSTRUCTING A PATIENT-SPECIFIC SURGICAL GUIDE

FIELD OF THE INVENTION

The invention relates to a method for constructing a patient-specific surgical guide.

BACKGROUND OF THE INVENTION

Patient-specific surgical guides become more and more used in dentistry or orthopedic surgery, for example in view of implanting total knee prosthesis.

A patient-specific guide is generated by an additive manufacturing technique (e.g. stereolithography or selective laser sintering) by including two kinds of elements:
  contact elements intended to match an anatomical structure (e.g. a bone) to be treated; and
  guiding elements such as drill guides, saw guides, or milling guides, intended to guide a surgical instrument in order to implant the required prosthesis once the patient-specific guide is positioned onto the anatomical structure of the patient. The planning of the position of the guiding elements corresponds to the planning of the prosthesis implantation.

The contact elements are chosen so as to provide a unique and stable position of the guide with respect to the anatomical structure.

FIG. 4 is a schematic view of an example of a patient-specific guide 1 positioned onto a patient's anatomical structure 2.

The guide 1 comprises a contact element 11 having a surface in contact with the anatomical structure 2, a guiding element 12 (in the form of a slot) for a saw blade and a guiding element 13 (in the form of a cylinder hole) for a drill. The position and orientation of the guiding elements 12, 13 with respect to the anatomical structure depends on the position and orientation of the prosthesis that is to be implanted.

WO 93/25157 describes a method for constructing a patient-specific surgical guide.

A 3D medical image (e.g. CT or MRI) of an anatomical structure of the patient is first segmented so as to reconstruct the anatomical structure, i.e. to form a 3D model of the anatomical structure. Such a 3D model is a representation of the 3D surface of the anatomical structure (for example using triangular facets) or a representation of the volume of the anatomical structure (for example using voxels) which implicitly defines its surface.

Then, contact points and/or contact faces are defined on the surface of the reconstructed anatomical structure so as to provide unique and stable positioning of the guide.

On the other hand, the position of the guiding elements with respect to the anatomical structure is defined.

Then, the surgical guide is constructed by generating a rigid body including the guiding elements and the contact elements. By "rigid" is meant here that the guide is not intended to deform during the surgical intervention.

The surgical guide can then be produced by an additive manufacturing technique.

Such a method is long and expensive for the following reasons.

In practice, it involves several flows of data between a radiologist who has acquired the 3D medical image, an expert center that carries out segmentation of the 3D medical image and planning of the surgical guides, and the surgeon who has ordered the patient-specific guide.

Typically, at least four flows of data and/or material are to be considered in such a process:

(A) The 3D medical image is sent by the radiologist to the expert center that carries out a segmentation of the 3D medical image so as to reconstruct the anatomical structure and determines a planning comprising a proposed position of implant and of the guiding elements.

The expert center usually comprises experts (engineers and/or technicians) in the processing of medical images.

The experts use specific tools for facilitating the segmentation of the images.

However, since the 3D medical image usually comprises a plurality of slices—typically from 150 to 200 slices—an error in the segmentation of only one slice may generate a large error in the final result.

Hence, the segmentation cannot be completely carried out automatically, and the expert has to segment manually at least the regions of the 3D medical image where the greyscale impedes an automatic recognition of the pixels between bone and soft tissues.

Such a manual segmentation is time-consuming (sometimes several hours) and increases the cost of the surgical guide.

The planning is usually based on standard default parameters.

(B) The expert center sends the planning to the surgeon.

(C) The surgeon checks and, if necessary, modifies the planning.

However, depending on the format of the planning data provided by the expert center, it may be difficult and unpractical for the surgeon to modify the planning. In particular, the 3D bone model that is obtained by the segmentation of the 3D medical image is not a medical image, which requires the surgeon to carry out the planning on an image that is not familiar to him.

Hence, the surgeon may be incited to accept the planning as provided by the expert who is usually not a surgeon; this situation is not satisfactory in terms of involvement of the surgeon in the planning step and more specifically in terms of responsibility.

(D) Based on the planning and the segmented image, the expert center constructs the surgical guide.

Said construction typically relies on the subtraction of the volume of a body comprising the guiding elements and intersecting the anatomical structure on the one hand, and of the volume of the anatomical structure.

Then, the expert center manufactures the guide (or orders it to a dedicated manufacturing center) and sends it to the surgeon.

Documents U.S. Pat. No. 8,092,465 and US 2009/138020 describe such a process.

The at least partially manual segmentation that is required to construct the 3D model of the anatomical structure may take several hours and thus contributes to a high cost of the 3D model.

Besides, the above-described multiple flows of data are time-consuming and unpractical.

In addition, the 3D bone model that is provided to the surgeon is not a medical image, which requires the surgeon to carry out the planning on an image that is not familiar to him.

BRIEF DESCRIPTION OF THE INVENTION

A goal of the invention is to provide a method for constructing a patient-specific surgical guide that overcomes the drawbacks of the existing solutions.

In particular, this method should be less expensive and time-consuming as known methods, while ensuring the accuracy of the definition of the contact elements.

In addition, the method should require less data flows than known methods. In particular, the method should not require any processing of the images by an expert center and should allow the surgeon to work on a type of images that is familiar to him or her and to get a more straightforward understanding of the information provided to him or her.

To that end, the invention provides a method for constructing a patient-specific surgical guide comprising at least one contact element comprising a contact surface intended to match an anatomical structure to be treated in view of implantation of an implant and at least one guiding element for guiding a surgical instrument to treat said anatomical structure, said method comprising:

receiving a non-segmented 3D medical image of the anatomical structure of the patient;

determining, in said non-segmented 3D medical image, an anatomical referential of the patient;

based on said anatomical referential, positioning an implant model in the non-segmented 3D medical image;

adjusting at least one of: a type, a size, a position and an orientation of the implant model with respect to the anatomical structure in the non-segmented 3D medical image;

recording planning data including said adjusted type, size, position and orientation of the implant model;

using a patient-specific surgical guide adapted to carry out implantation of the implant, said patient-specific surgical guide being constructed using the planning data.

By "anatomical structure" is meant in the present text a substantially rigid structure, such as a bone or cartilage, whose shape can be determined on medical images and whose shape will not substantially evolve between the acquisition of the medical images and the use of the guide. It can be but is not limited to an osseous structure.

By "anatomical referential" is meant in the present text a coordinates system based on the patient's anatomy, allowing planning the position and orientation of the implant with respect to the anatomical structure. Depending on the application, said anatomical referential may be constructed from anatomical references or landmarks acquired on the 3D medical image (this is in particular the way of creating an anatomical referential in orthopedic applications). In some applications (e.g. in dentistry), it is not necessary to specifically acquire anatomical landmarks; the anatomical referential can be determined directly from the native orientation of the 3D medical image.

According to an embodiment, the 3D medical image is a 3D medical image directly obtained by Computed Tomography. Alternatively, the 3D medical image may be a 3D medical image directly obtained by Magnetic Resonance Imaging.

According to an embodiment, the method further provides control elements for interactively modifying at least one of a type, a size, a position and an orientation of the implant.

According to an embodiment, the implant is a femoral component or a tibial component of a knee prosthesis.

According to an advantageous embodiment, the surgical plan is used as follows for the construction of the patient-specific surgical guide.

At least one region of interest containing a portion of the external surface of the anatomical structure intended to match a respective contact element of the surgical guide is determined based on the planning data. The 3D medical image is segmented only in said at least one determined region of interest so as to locally reconstruct the external surface of the anatomical structure. The contact surface of the contact element is computed from said reconstructed local surface of the anatomical structure; the at least one contact element is constructed to include the contact surface. The position of the at least one guiding element is determined with respect to the anatomical structure. The surgical guide is constructed by generating a rigid body including the at least one guiding element and said at least one contact element.

By requiring only local segmentation of the 3D medical image (i.e. the segmentation being limited to the determined region(s) of interest), the construction of the guide is much quicker than conventional methods.

In addition, since the segmentation is limited to small regions of the image, one can afford a better accuracy of this operation.

Besides, said method provides a deeper involvement of the surgeon in the planning process, which is also beneficial to the accuracy of the guide and of the subsequent implantation procedure.

According to an embodiment, the determination of the at least one region of interest is carried out automatically. Said at least one determined region of interest can further be adjusted interactively by a user.

According to an embodiment, the automatic determination of the at least one region of interest is based on anatomical landmarks.

According to an embodiment, the determination of the at least one region of interest is carried out interactively.

According to an embodiment, at least two separate regions of interest are determined in the 3D image, each region of interest containing a portion of the external surface of the anatomical structure intended to match a respective contact element of the surgical guide.

According to an embodiment, the construction of the contact element comprises extruding a part of the rigid body until the computed contact surface.

According to an embodiment, the contact surface is computed as being the reconstructed local surface of the anatomical structure.

According to an embodiment, the construction of the contact element comprises extruding a part of the rigid body toward the anatomical structure and subtracting the anatomical structure from said extruded part until the computed contact surface.

According to an embodiment, the method further comprises defining the guide as an addition of at least two elements, wherein at least one element has at least one determined degree of freedom with respect to the anatomical structure.

Another aspect of the invention is a computer program product comprising computer-readable instructions which, when loaded and executed on a suitable system, perform the steps of the method described above.

Another object of the invention is a method for constructing a patient-specific surgical guide comprising at least one contact element comprising a contact surface intended to match an anatomical structure to be treated in view of implantation of an implant and at least one guiding element for guiding a surgical instrument to treat said anatomical structure, said method comprising:

receiving planning data including a type, size, position and orientation of the implant, wherein the planning data has been created from a non-segmented 3D medical image;

based on the planning data, determining at least one region of interest containing a portion of an external surface of the anatomical structure intended to match a respective contact element of the surgical guide;

segmenting the 3D medical image only in said at least one determined region of interest so as to locally reconstruct the external surface of the anatomical structure;

computing the contact surface of the contact element from said reconstructed local surface of the anatomical structure;

constructing the at least one contact element to include the contact surface;

defining the position of the at least one guiding element with respect to the anatomical structure;

constructing the surgical guide by generating a rigid body including the at least one guiding element and said at least one contact element.

BRIEF DESCRIPTION OF THE DRAWINGS

Other features and advantages of the invention will be apparent from the appended drawings, wherein.

DETAILED DESCRIPTION OF EMBODIMENTS OF THE INVENTION

Figures 1A, 1B:
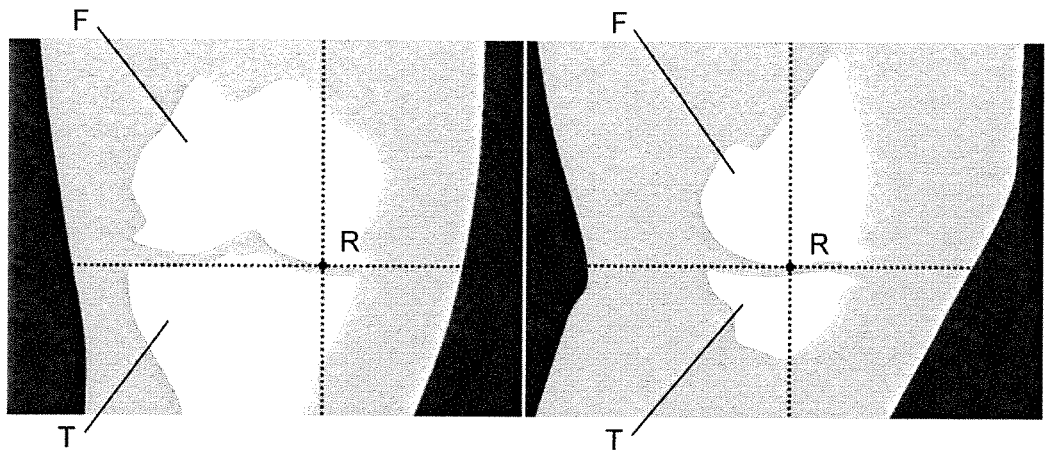
FIGS. 1A and 1B are schematic views showing non-segmented images on which anatomical references are selected.

The 3D medical image of the anatomical structure of the patient is acquired in a preliminary step that is not specifically included in the method according to the invention.

In this respect, said 3D medical image may be acquired at any time before carrying out this method, by any suitable technique such as Computed Tomography (CT) or Magnetic Resonance Imaging (MRI).

The method can be carried out by a computer system comprising at least one processor that is able to carry out the treatment of the 3D medical image and the construction of the elements of the guide. The system may also comprise a user interface comprising a display device, such as a screen, for displaying the 3D image so as to allow the user to select the region(s) of interest, if appropriate, and/or for visualizing the different elements of the guide during the construction of the guide. The user interface may further comprise controls allowing a user to interactively modify the surgical plan.

In the description that follows, the invention is mainly described with reference to the planning of the implantation of a knee prosthesis, the intervention comprising the implantation of a femoral implant and/or a tibial implant on a patient's knee.

However, the invention is not limited to this kind of implantation and can be implemented for constructing a patient-specific surgical guide adapted for the implantation of any other implant.

It is to be noted that the creation of the surgical plan is carried out on non-segmented 3D images, e.g. on 3D images as acquired by a 3D imaging device, or on 2D slices reconstructed in another direction than the one used for the acquisition, or on pseudo-radiographic images (a pseudo-radiographic image being a 2D image wherein each pixel integrates the information of the 3D image along a determined direction of integration). The way of computing pseudo-radiographic images is explained in patent application PCT/EP2014/074042, which is herein incorporated by reference.

The method thus allows the user to benefit from images that are familiar to him, since the non-segmented 3D images and the representation of the implant that are displayed are similar to radiographic images onto which the surgeon visualizes the implant one implanted. Hence, the understanding of the displayed image by the surgeon is more straightforward.

Determination of an Anatomical Referential

According to an embodiment (e.g. in dentistry), an anatomical referential is directly defined from the native orientation of the 3D medical image.

According to an alternative embodiment (e.g. in orthopedic surgery), anatomical references or landmarks are determined in the non-segmented 3D medical image in order to construct the anatomical referential.

The position and orientation of the implant will then be determined with respect to said anatomical referential.

The determination of the anatomical references can be carried out using any suitable technique such as selecting them in 2D slices of the 3D medical image, or selecting them in reconstructed images wherein each pixel of said reconstructed images integrates the information of a 3D image along a determined direction of integration, said determined direction of integration depending on the axis of the 3D image and possibly on the previously acquired anatomical landmarks.

According to an embodiment, said landmarks are detected automatically.

According to an alternative embodiment, said landmarks are positioned in the non-segmented 3D medical image by a surgeon.

Figures 2A, 2B, 2C:
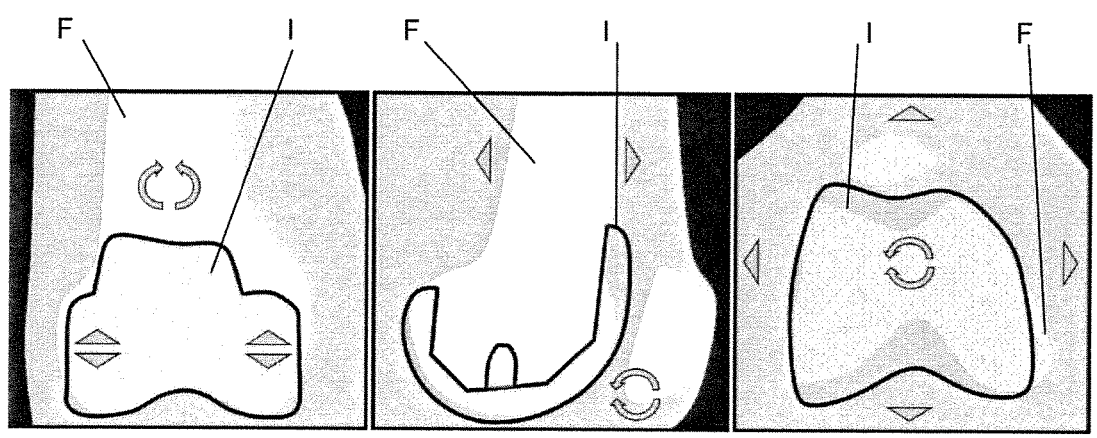
FIGS. 2A-2C are schematic drawings showing an example of a display comprising three images with implant and anatomical structures according to different views allowing the surgeon to modify the position and the orientation of the implant.

According to another embodiment, the landmarks are first detected automatically and displayed on the 3D medical image, and then interactively adjusted by the surgeon if required. In such a case, the interface comprises controls that allow said adjustment by the surgeon. FIGS. 2A-2C illustrate such controls (shown as arrows) that can be used by the surgeon to modify the planning.

For example, FIGS. 1A and 1B show images of a knee with a femur F and a tibia T according to two different views, on which an anatomical landmark R such as medial distal condyle can be selected.

Since the determination is made directly on the non-segmented 3D medical image, the anatomical landmarks can be determined by the surgeon without sending the 3D medical image to an expert center.

According to an advantageous embodiment, the anatomical landmark can be positioned automatically on the image, and then interactively adjusted by the surgeon. Displaying concurrently different views of the anatomical structure, as in FIGS. 1A and 1B, improves the accuracy of the determination of the anatomical landmarks.

Positioning of the Implant Model

Typically, the implant that is to be implanted is a conventional, not patient-specific, prosthesis component available in different sizes. However, patient-specific prosthesis components prepared with computer-assisted image methods can also be used.

Numerical models of the available implants, which have been computed previously (this computation not belonging to the invention), are provided in view of the planning procedure.

An initial planning of the position and orientation of the implant in a given size in the referential of the 3D medical image is carried out by any suitable technique such as using some default values to position the implant with respect to said anatomical landmarks.

Since this initial planning is performed on the non-segmented 3D medical image, it can be carried out by the surgeon without sending the 3D medical image to an expert center.

The method can be carried out by a planning system comprising at least one processor that is able to compute and update the non-segmented 3D image, and a display device, such as a screen, for displaying the non-segmented 3D image with a representation of the implant.

Adjustment of the Type, Size, Position and Orientation of the Implant

The initial planning may not be optimal. For example, the implant size may be larger or smaller than required. Also, the position and/or orientation of the implant may not be accurate enough.

Hence, at least one of the type, size, position and orientation of the implant can be adjusted, either automatically or interactively.

To that end, the initial implant model can be replaced in the 3D medical image by a new implant model corresponding to a different implant type or having a different size.

In a preferred embodiment of the method, one or more controls are displayed to modify interactively the size, type, position and/or orientation of the implant. Some controls can be displayed or used directly on the images.

There are a number of ways of displaying controls on the interface, such as buttons, or clicking and dragging on the implant to translate it, or clicking and dragging around the implant to rotate it.

FIGS. 2A to 2C show different views of the implant I and the anatomical structure F displayed on a computer screen, comprising interactive controls (represented by arrows) that can be used by the surgeon to adjust the position and/or orientation of the implant. If the position and/or orientation of the implant is modified in one view, the other views may be updated based on the new position and/or orientation of the implant.

Figure 3:
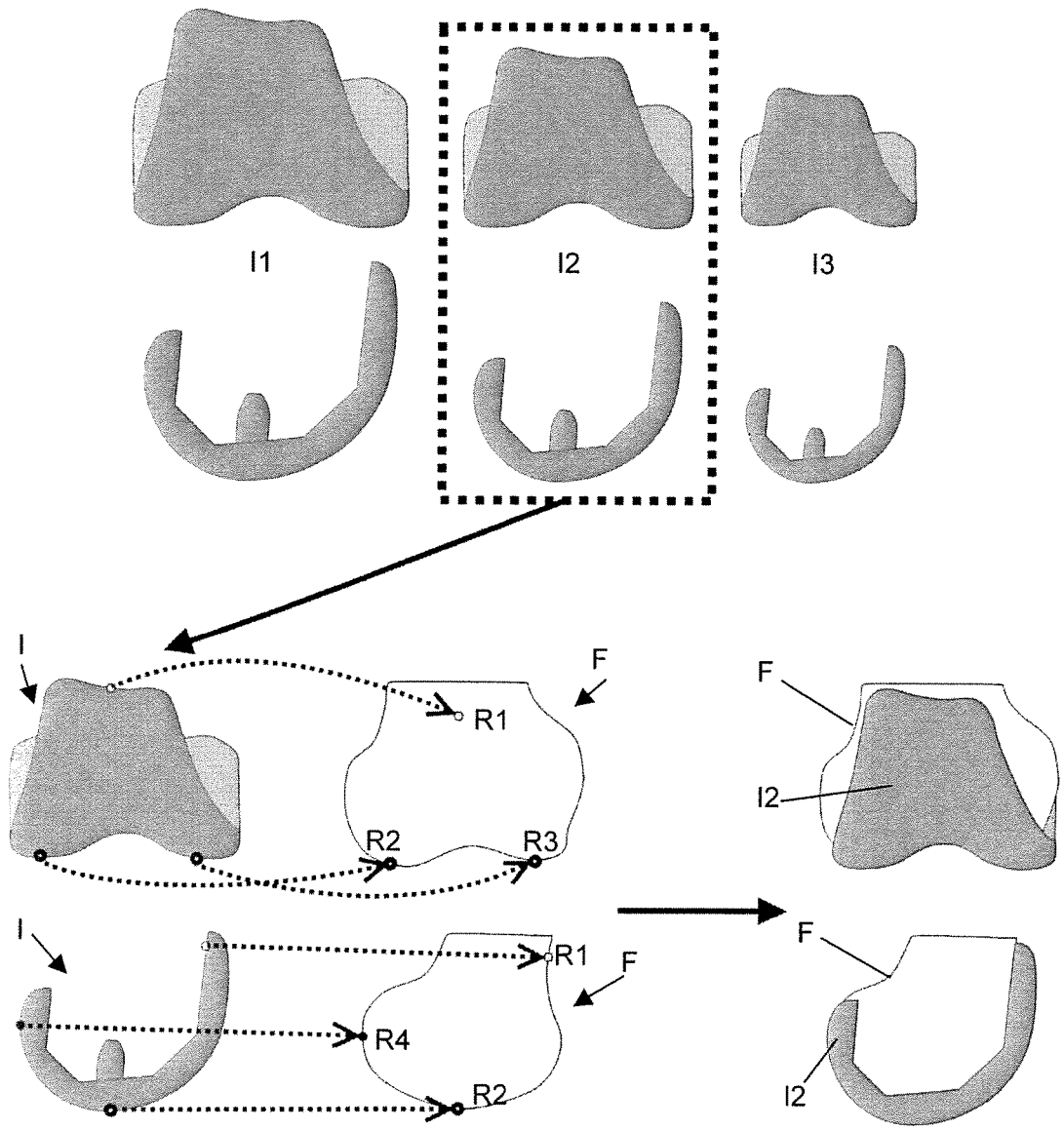
FIG. 3 is a schematic view illustrating the selection of the implant size and the implant positioning on the non-segmented images thanks to the selected anatomical references during the planning step.
Figure 4:
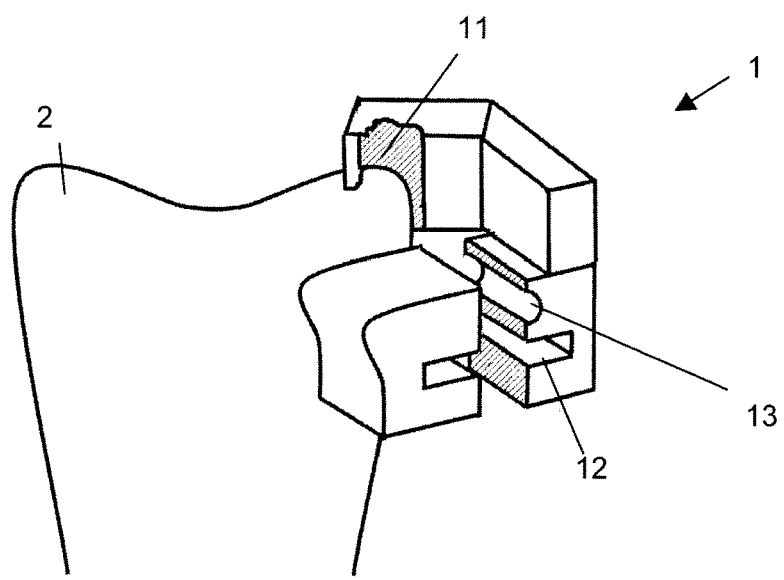
FIG. 4 is a schematic view of a patient-specific guide positioned onto a patient's anatomical structure.

FIG. 3 illustrates an exemplary embodiment of the selection of an optimal implant size.

In this example, implants I1, I2 and I3 (which are seen according two different views in the upper part of FIG. 3) have decreasing sizes.

As shown in the left lower part of FIG. 3, reference points of the implants are compared to respective anatomical references R1-R4 on the anatomical structure (here, femur F), according to different views.

The implant I2, which is the one matching best the anatomical structure F, is selected as the implant to be implanted in the patient. The anatomical references R1-R4 are also used to position the implant model with respect to the anatomical structure in the image (right lower part of FIG. 3).

Then, the position and orientation of the implant with respect to the anatomical structure may further be adjusted.

Of course, the size, type, position and orientation may be adjusted concurrently or sequentially in any order. In addition, the adjustment may comprise successive trials of implants of different types or sizes.

Once the surgeon considers that the type, size, position and orientation of the implant is satisfactory, he validates the planning and records the surgical plan.

The output of the above-described method is thus a surgical plan containing planning data including the type, size, position and orientation of the implant to be implanted on the anatomical structure of the patient. The planning data may also comprise definition of the parameters of the surgical procedure (e.g. position and orientation of cutting planes and/or drilling axes) that will be required to place the implant on the anatomical structure.

This surgical plan is then used for the construction of a patient-specific surgical guide adapted to be used for implanting the planned implant.

To that end, the surgical plan may be sent (e.g. mailed in an electronic storage medium such as a CD-ROM, a DVD-ROM or a memory device, or sent via Internet) to a design center capable of treating the surgical plan to construct the surgical guide.

Otherwise, the surgeon may use a dedicated computer program to construct a computer model of the surgical guide and then have the surgical guide manufactured based on said model.

Construction of the Patient-specific Surgical Guide

Based on the above-described surgical plan, the construction of the patient-specific surgical guide may comprise the following steps.

Determination of at Least One Region of Interest

One or more regions of interest are defined in the 3D medical image.

Said one or more regions of interest can be automatically determined, for example based on: the position of the anatomical landmarks; a first rough automated segmentation; the planning data (including the type, size, position and orientation of the implant to be implanted and the parameters of the surgical procedure such as the position and orientation of cutting planes and/or drilling axes) and/or the position of other elements of the patient-specific guide.

A first level of information is that the regions of interest must be placed outside of the volume of the implant set on the 3D image because the goal is to create guiding slots to cut the planes on which the implant will lie. Moreover, it is important to position the regions of interest that will define the contact elements as close as possible to the implant, in order to minimize the invasiveness of the guide. Some landmarks and directions can be defined on the implant. Then some geometrical rules are applied to build several regions of interest from said landmarks and directions. As an example, a region of interest having a size of ten millimeters can be defined to have a center located at a distance of six millimeters from a landmark of the implant (that is for example located on its internal side, at the intersection of the anterior plane and the anterior chamfer plane of the implant), said region of interest having a preferred direction orthogonal to said anterior chamfer plane.

Advantages of said automatic determination of said one or more regions of interest include a reduced time to design, which allows obtaining cheaper guides.

In addition, automatic determination allows the technician to focus on what can really affect guide performance, i.e. performing or checking the segmentation in the local regions of interest.

According to an embodiment, e.g. in the case of implantation of a knee prosthesis, the planned cutting planes can be used to define the region(s) of interest for the cutting guide. For example, the planned distal femoral cutting plane can serve as a basis for defining the region(s) of interest on the distal part of the femur; the planned anterior femoral cutting plane can serve as a basis for defining the region(s) of interest on the anterior cortical bone; and the planned tibial cutting plane may serve as a basis for defining the region(s) of interest on the tibial plateaus.

Such use of the planning data is advantageous in that it allows constructing minimally invasive guides since the region(s) of interest is(are) as close as possible to the position of the planned implant. As a consequence, the amount of soft tissues to be removed—such removal being invasive—is minimized.

According to an embodiment, e.g. in dentistry, the drilling parameters (orientation, length and entry point) and a panoramic curve defined during the planning process can be used to determine the region(s) of interest for the drilling guide. In such way, the zones (teeth, gums and bone) intended to support the guide can be determined automatically.

According to an embodiment, the one or more regions of interest can be defined interactively, for example by displaying both the region of interest and the 3D medical image in the same view.

Methods for displaying 3D medical images are well known, and include volume rendering.

Figure 5:
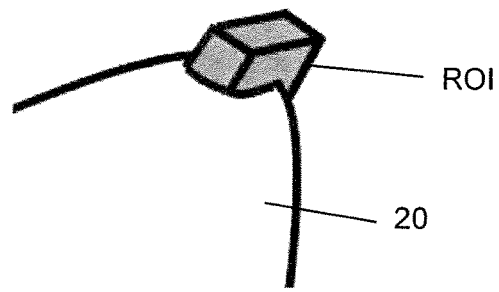
FIG. 5 is a schematic view showing the simultaneous display of a region of interest and of volume rendering of the anatomical structure.

FIG. 5 is a schematic view showing the simultaneous display of a region of interest (referred to as ROI) and of volume rendering 20 of the anatomical structure.

Another possible way of defining a region of interest interactively includes displaying one or more 2D slices of the 3D medical images in the region of interest.

In such case, it may be advantageous that said 2D slices of the 3D medical images in the region of interest are some of the slices on which the local reconstruction of the external surface of the anatomical structure will be subsequently performed.

Figure 6:
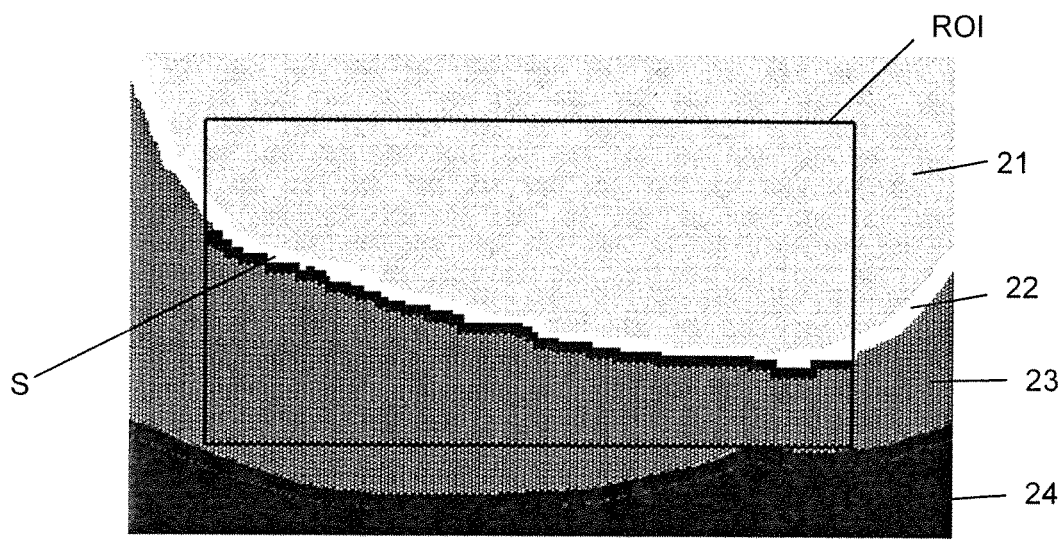
FIG. 6 is a schematic view of a local segmentation interface wherein the boundaries of the region of interest are displayed.

FIG. 6 is a schematic view of a local segmentation interface, wherein the boundaries of the region of interest ROI are displayed on a slice comprising different greyscale regions 21, 22, 23, 24. Region 21 corresponds to the anatomical structure and region 22 corresponds to the external surface of the anatomical structure, whereas regions 23 and 24 do not belong to the anatomical structure.

The 3D image is segmented inside said region of interest. The segmentation is represented by a surface S that is superimposed with the region 22.

In a preferred embodiment, 2D slices are reconstructed and displayed in the region of interest only. One can scroll the 3D image in this limited area only. A 2D slice appears as a small image with rows along a direction Y and columns along a direction X and the local segmentation process consists in selecting a curve that defines a function $Y=f(X)$. So one wants to identify one pixel per vertical line. For that purpose, the user can click and drag the mouse to change the horizontal position of the points hovered by the mouse, which makes for very fast manual adjustments. Multiple other standard tools can be used for such semi-automated local segmentation (thresholding, spline interpolation, snakes, region growing, etc.). Typically, the curve obtained in one 2D slice serves as a basis for the next slice, and the process is repeated.

Because the ROI is relatively small, the edges of the anatomical structure inside the ROI have usually a similar appearance with respect to the surrounding soft tissues. Therefore, standard adaptive algorithms will have increased chances to be successful and offer fully automated and accurate segmentation. For example algorithms that search automatically for an optimal threshold that define the searched structure, with small variations from one area to the neighboring one can be extremely successful. There exists a very large number of automated segmentation methods of 2D and 3D images. For the vast majority of them, working in a small and relatively homogeneous sub-volume increases significantly their chances of success. A reasonable assumption is also to search for series of curves $Y=f(X)$ as described above, which in 3D translates to the search of a function $Z=f(X,Y)$, and this represents very useful a priori information for automated segmentation algorithms (at the opposite of global segmentation methods that have very poor assumptions about the topology of the searched structure).

Moreover, because the ROI is small, the user can supervise the process of interactive or automated segmentation with a high degree of attention, which makes it safe.

Advantages of said interactive or automated determination of said one or more regions of interest include the fact that the definition of individual anatomy in a small area is made easier, faster and safer than a complete anatomical structure.

According to an embodiment, said one or more regions of interest can be automatically defined and further be fine-tuned interactively, which aggregates the advantages of automatic determination and interactive determination.

Local Reconstruction of the External Surface of the Anatomical Structure

After determination of the at least one region of interest, the 3D medical image is segmented in said determined region of interest so as to locally reconstruct the external surface of the anatomical structure.

This is a so-called local segmentation since the segmentation of the 3D image is carried out only in the determined region(s) of interest and no segmentation is carried out in the other regions of the 3D image.

Advantages of said local segmentation include a reduced time to perform and check segmentation since the amount of data to be treated is significantly reduced.

In addition, since the region(s) to be segmented are limited, the technician can focus on what can really affect guide performance, i.e. performing or checking the segmentation in the local regions of interest.

Besides, interactive reconstruction of the external surface of the anatomical structure is made easier. Indeed, very often and as illustrated in FIG. 5, the local external surface of the anatomical structure can be clearly determined in a single set of parallel images, with a sharp contrast between the anatomical structure (regions 21, 22) and its surroundings (regions 23, 24).

To the contrary, in view of a global segmentation of the 3D medical image, at least two different sets of parallel images are required.

Another advantage of carrying out only a local segmentation is that automated reconstruction of the external surface of the anatomical structure is made easier. Indeed, very often, the range of values of the 3D medical images can vary greatly between different parts of the anatomical structure, e.g. cortical bone density is much higher than the density of bone on the femur distal condyles. In view of automatically computing an accurate global segmentation, advanced algorithms with adaptive thresholds would be required and usually fail. By contrast, since local segmentation involves only a limited part of the 3D image, it is less subjected to variation of the range of values and can thus be carried out by simpler algorithms.

Automated reconstruction of the external surface of the anatomical structure is also made easier on a selected slice of the 3D image. Indeed, as already explained above, the local external surface of the anatomical structure can be clearly determined in a single set of parallel images, with a sharp contrast between the anatomical structure and its surroundings.

Automated reconstruction of the external surface of the anatomical structure is further rendered easier by the fact that, very often, the local external surface of the anatomical structure can be made to follow some general pattern on this single set of parallel images. This general pattern can generally be the same for all patients, which helps in making a robust algorithm. The segmentation can also generally be made to vary little between the slices, which further helps in making a robust algorithm.

Computation of the Contact Surface(s)

The contact surface on which the contact element of the patient-specific guide will be based can be the local reconstruction of the external surface of the anatomical structure.

However, it may be interesting to apply some transformations to said local reconstruction of the external surface of the anatomical structure.

Examples of said transformations include:
cropping, which sets on a given plane the local reconstruction which is on one side of the plane. It may prevent the patient-specific guide from being cut by a saw blade during surgery.
smoothing. It may reduce the size of the output and prevent sharp edges.
reduction of the number of surface descriptors (e.g. number of triangles or number of splines) without smoothing. It may reduce the size of the output.
offset, e.g. to adapt to some specific manufacturing machine, or to add some play where the assembly of the guide and the anatomical structure would otherwise be over-constrained.
other transformations, which may add some property to the guide, e.g. transformations which confer to the guide a preferred insertion direction with respect to a contact surface.

Definition of the Contact Element(s)

As explained previously, the contact surface of the contact element is the reconstructed external surface of the anatomical structure (possibly after a transformation such as the ones described above).

Said contact surface is thus defined by a closed mesh.

According to an embodiment, the contact element may be computed by removing said closed mesh from uncut contact elements which intersect said closed mesh. Said uncut contact elements may be the whole patient-specific guide before removing the closed mesh. It is possible to do so in this method, by computing a closed mesh bounded by the contact surface on one side, and the region of interest on the other sides.

But Boolean operations on meshes are sometimes hard to implement.

To avoid said Boolean operations on meshes, it is possible, according to an alternative embodiment, to extrude a part of the rigid body forming the guide until the contact surface.

Definition of the Guiding Element(s)

Guiding elements have a shape that guides a surgical instrument, such as a slot to guide a saw blade, or a cylinder hole to guide a drill or a pin.

The construction of a guiding element usually involves digging a shape into a rigid body, but it can sometimes also involve the addition of matter to the guide, for example so that the drill bumps into a mechanical stop.

Construction of the Guide

The guide is defined as the sum of the guiding elements, the contact elements, and possibly some other elements such as junctions.

Guiding elements can also be contact elements (i.e. a single element may fulfill both contact and guiding functions), and it is possible to consider only one element which is the whole guide.

A preferred construction of the guide comprises an element-by-element construction of the guide, wherein each contact or guiding element is automatically placed and sized so that mechanical properties (e.g. stiffness), planning properties (e.g. position and orientation of a cutting plane, or position and orientation of a drill) and integrity of the guide (e.g. the final design must be printed as one single element) are fulfilled.

The shape (e.g. size in some directions, such as length, height, width), position, and/or orientation of some elements can be modified interactively.

Some modifications to the shape of some elements may be blocked or bounded (e.g. prevented from downsizing in order to ensure minimum stiffness of the guide, prevented from some rotations and translations of a guiding element in order to be consistent with planning).

The elements which propose no modification to the user are ideally automatically built with no interaction from the user, letting the user focus on the elements which he could modify.

At last, the guide is the addition of these elements.

In another preferred embodiment, the guide is defined as a parametric model, wherein its parameters define geometrical properties of its elements. Said geometrical properties may be typically height, length and depth of each block and junction element that will constitute the guide. Some parameters may be fixed, for example to prevent for too small thickness that might create weaknesses. Other parameters may be variable within a range to prevent from abnormal guides to be designed. Obviously, the guide will contain also some specific blocks that contain the contact elements and blocks that contain the guiding elements. But only the definition of the contact elements and the guiding elements is not sufficient to define entirely a guide. The parameters of the parametric model are then adjusted using geometrical rules that depend on data specific to the case. Said specific data may be landmarks defined on the anatomical structure, or landmarks defined on the implant once it is in the planned position. The selection of the parametric model and the rules for adjusting the parameters of the guide will constitute a particular choice of design. Multiple choices and design solutions are possible.

Then the guide can be manufactured by any suitable technique, such as stereolithography or selective laser sintering.

The guide is then received by the surgeon or another person of the medical staff in view of being used by the surgeon to carry out the implantation procedure.

REFERENCES

WO 93/25157
U.S. Pat. No. 8,092,465
US 2009/138020

The invention claimed is:

1. A method for constructing a patient-specific surgical guide comprising at least one contact element comprising a contact surface intended to match an anatomical structure to be treated in view of implantation of an implant and at least one guiding element for guiding a surgical instrument to treat said anatomical structure, said method comprising:
   receiving a non-segmented 3D medical image of the anatomical structure of the patient;
   determining, in said non-segmented 3D medical image, an anatomical referential of the patient;
   based on said anatomical referential, positioning an implant model in the non-segmented 3D medical image;
   adjusting at least one of: a type, a size, a position and an orientation of the implant model with respect to the anatomical structure in the non-segmented 3D medical image;
   recording planning data including said adjusted type, size, position and orientation of the implant model;
   using a patient-specific surgical guide adapted to carry out implantation of the implant, said patient-specific surgical guide being constructed using the planning data, wherein the determining, positioning and adjusting steps are implemented without constructing any model of the anatomical structure.

2. The method of claim 1, wherein the anatomical referential is constructed from anatomical references of the patient acquired in the non-segmented 3D medical image.

3. The method of claim 1, wherein the anatomical referential is determined directly from a native orientation of the 3D medical image.

4. The method of claim 1, wherein the 3D medical image is a 3D medical image directly obtained by Computed Tomography.

5. The method of claim 1, wherein the 3D medical image is a 3D medical image directly obtained by Magnetic Resonance Imaging.

6. The method of claim 1, further providing control elements for interactively modifying at least one of a type, a size, a position and an orientation of the implant.

7. The method of claim 1, wherein the implant is a femoral component or a tibial component of a knee prosthesis.

8. The method of claim 1, wherein the construction of the patient-specific surgical guide comprises:
   based on the planning data, determining at least one region of interest containing a portion of an external surface of the anatomical structure intended to match a respective contact element of the surgical guide;
   segmenting the 3D medical image only in said at least one determined region of interest so as to locally reconstruct the external surface of the anatomical structure;
   computing the contact surface of the contact element from said reconstructed local surface of the anatomical structure;
   constructing the at least one contact element to include the contact surface,
   defining the position of the at least one guiding element with respect to the anatomical structure;
   constructing the surgical guide by generating a rigid body including the at least one guiding element and said at least one contact element.

9. The method of claim 8, wherein the determination of the at least one region of interest is carried out automatically.

10. The method of claim 9, wherein the at least one determined region of interest is adjusted interactively by a user.

11. The method of claim 9, wherein the automatic determination of the at least one region of interest is based on anatomical landmarks.

12. The method of claim 8, wherein the determination of the at least one region of interest is carried out interactively.

13. The method of claim 8, wherein at least two separate regions of interest are determined in the 3D image, each region of interest containing a portion of the external surface of the anatomical structure intended to match a respective contact element of the surgical guide.

14. The method of claim 8, wherein the construction of the contact element comprises extruding a part of the rigid body until the computed contact surface.

15. The method of claim 8, wherein the contact surface is computed as being the reconstructed local surface of the anatomical structure.

16. The method of claim 8, wherein the construction of the contact element comprises extruding a part of the rigid body toward the anatomical structure and subtracting the anatomical structure from said extruded part until the computed contact surface.

17. The method of claim 8, comprising defining the guide as an addition of at least two elements, wherein at least one element has at least one determined degree of freedom with respect to the anatomical structure.

18. Computer program product comprising computer-readable instructions which, when loaded and executed on a suitable system, perform the following steps:
   receiving a non-segmented 3D medical image of the anatomical structure of the patient;
   determining, in said non-segmented 3D medical image, an anatomical referential of the patient;
   based on said anatomical referential, positioning an implant model in the non-segmented 3D medical image;
   adjusting at least one of: a type, a size, a position and an orientation of the implant model with respect to the anatomical structure in the non-segmented 3D medical image;
   recording planning data including said adjusted type, size, position and orientation of the implant model;
   wherein the determining, positioning and adjusting steps are implemented without constructing any model of the anatomical structure.

19. A method for constructing a patient-specific surgical guide comprising at least one contact element comprising a contact surface intended to match an anatomical structure to be treated in view of implantation of an implant and at least one guiding element for guiding a surgical instrument to treat said anatomical structure, said method comprising:
   receiving planning data including a type, size, position and orientation of the implant, wherein the planning data has been created from a non-segmented 3D medical image;
   based on the planning data, determining at least one region of interest containing a portion of an external surface of the anatomical structure intended to match a respective contact element of the surgical guide;

segmenting the 3D medical image only in said at least one determined region of interest so as to locally reconstruct the external surface of the anatomical structure;

computing the contact surface of the contact element from said reconstructed local surface of the anatomical structure;

constructing the at least one contact element to include the contact surface;

defining the position of the at least one guiding element with respect to the anatomical structure;

constructing the surgical guide by generating a rigid body including the at least one guiding element and said at least one contact element.

* * * * *